US012582648B2

(12) United States Patent
Lecomte et al.

(10) Patent No.: US 12,582,648 B2
(45) Date of Patent: Mar. 24, 2026

(54) METHOD FOR TREATING CENTRAL NERVOUS SYSTEM DISORDERS USING DOPAMINE D3 PARTIAL AGONISTS

(71) Applicant: BIOPROJET Pharma, Paris (FR)

(72) Inventors: Jeanne-Marie Lecomte, Paris (FR); Jean Charles Schwartz, Paris (FR); Isabelle Berrebi-Bertrand, Pace (FR); Stéphane Krief, Rennes (FR); Xavier Ligneau, Saint-Grégoire France (FR); Isabelle Lecomte, Paris (FR)

(73) Assignee: BIOPROJET PHARMA, Paris (FR)

( * ) Notice: Subject to any disclaimer, the term of this patent is extended or adjusted under 35 U.S.C. 154(b) by 631 days.

(21) Appl. No.: 17/922,767

(22) PCT Filed: May 4, 2021

(86) PCT No.: PCT/EP2021/061689
§ 371 (c)(1),
(2) Date: Nov. 1, 2022

(87) PCT Pub. No.: WO2021/224235
PCT Pub. Date: Nov. 11, 2021

(65) Prior Publication Data

US 2023/0165852 A1 Jun. 1, 2023

(30) Foreign Application Priority Data

May 4, 2020 (EP) .................................... 20305429

(51) Int. Cl.
*A61K 31/495* (2006.01)
*A61P 25/16* (2006.01)
*A61P 25/28* (2006.01)

(52) U.S. Cl.
CPC ............ *A61K 31/495* (2013.01); *A61P 25/16* (2018.01); *A61P 25/28* (2018.01)

(58) Field of Classification Search
CPC ........ A61K 31/495; A61P 25/16; A61P 25/28; A61P 25/00
See application file for complete search history.

(56) References Cited

FOREIGN PATENT DOCUMENTS

| | | | |
|---|---|---|---|
| EP | 1 591 455 | A1 | 11/2005 |
| WO | 2007/113260 | A1 | 10/2007 |
| WO | 2007/148208 | A2 | 12/2007 |

OTHER PUBLICATIONS

Vippagunta SR, Brittain HG, Grant DJ. Crystalline solids. Adv Drug Deliv Rev. May 16, 2001;48(1):3-26.*
International Search Report issued in PCT/EP2021/061689, dated Jul. 28, 2021, 4 total pages.
Written Opinion of the International Searching Authority issued in PCT/EP2021/061689, dated Jul. 28, 2021, 7 total pages.
European Search Report issued in Application No. 20305429.1, dated Nov. 9, 2020.
Di Ciano et al. "Occupancy of dop''amine D2 and D3 receptors by a novel D3 partial agonist BPI.4979: a [11C]-(+)-PHNO PET study in humans", Neuropsychopharmacology, 2019, vol. 44, No. 7, pp. 1284-1290.
Clemens et al., "D3 and D1 receptors: The Yin and Yang in the treatment of restless legs syndrome with dopaminergics", Advances in Pharmacology, 2019, vol. 84, pp. 79-100.
Barroso-Chinea et al., "DRD3 (dopamine receptor D3) but not DRD2 activates autophagy through MTORC1 Inhibition preserving protein synthesis", Autophagy, 2019, 18 total pages.
Bézard et al., "Attenuation of levodopa-induced dyskinesia by normalizing dopamine D3 receptor function", Nature Medicine, Jun. 2003, vol. 9, No. 6, pp. 762-767.
Carlsson et al., "Seasonal and Circadian Monoamine Variations in Human Brains Examined Post Mortem", Acta Psychiatrica Scandinavica, Psychopathology of affective disorders, Mar. 1980, vol. 61, Issue S280, pp. 75-85.
Hening et al., "An Update on the Dopaminergic Treatment of Restless Legs Syndrome and Periodic Limb Movement Disorder", Sleep, 2004, vol. 27, No. 3, pp. 560-583.
Luis-Ravelo et al., "Pramipexole reduces soluble mutant huntingtin and protects striatal neurons through dopamine D3 receptors in a genetic model of Huntington's disease", Experimental Neurology, 2018, vol. 299, pp. 137-147.
Akpinar, "Treatment of Restless Legs Syndrome With Levodopa Plus Benserazide", Arch Neurol., Nov. 1982, vol. 39, No. 11, Abstract provided.
Wang et al., "A pivotal role of FOS-mediated BECN1/Beclin 1 upregulation in dopamine D2 and D3 receptor agonist-induced autophagy activation", Autophagy, Nov. 2015, 1:11, pp. 2057-2073.
Wang et al., "Dopamine Receptor Subtypes Differentially Regulate Autophagy", International Journal of Molecular Sciences, 2018, vol. 19, 1540, pp. 1-16.

* cited by examiner

*Primary Examiner* — Sahar Javanmard
(74) *Attorney, Agent, or Firm* — NIXON & VANDERHYE

(57) ABSTRACT

Disclosed is a method of using D3 partial agonists for treating or inhibiting the restless leg syndrome, binge eating, essential tremor and neurodegenerative diseases, in particular D3 partial agonists/D2 antagonists.

4 Claims, 2 Drawing Sheets

METHOD FOR TREATING CENTRAL NERVOUS SYSTEM DISORDERS USING DOPAMINE D3 PARTIAL AGONISTS

CROSS-REFERENCE TO RELATED APPLICATION(S)

This application is the U.S. national phase of International Application No. PCT/EP2021/061689 filed May 4, 2021, which designated the U.S. and claims priority to EP 20305429.1 filed May 4, 2020, the entire contents of each of which are hereby incorporated by reference.

BACKGROUND OF THE INVENTION

Field of the Invention

The Restless Leg Syndrome (RLS, or Willis Ekbom Disease WED) is a sleep-related movement disorder with a prevalence in the population ranging from 9.4% to 15%. It occurs mostly when the patient is lying which manifests by the urge to move the legs. This is associated with abnormal sensations in the limbs that are reduced during motor activity and with a circadian pattern that peaks at night.

It is a disabling central nervous system (CNS) disorder, and there is evidence that supports the use of dopamine agonists. Intriguingly, hypothalamic dopamine has a circadian rhythm with lowest concentrations observed at night when RLS emerges (Carlsson et al., Psychopathology of affective disorders, 75-85, 1980). Further, primary treatment for RLS involves dopamine D2/D3 full agonists: The first evidence that stimulation of dopamine receptors was beneficial in RLS was a trial with five patients showing that treatment with L-dopa plus benserazide, an indirect full dopamine agonist already known to compensate the dopamine deficit in Parkinson's disease patients, completely resolved the RLS symptoms in these five patients (Akpinar, S. Arch. Neurol., 1982, 39(11), 739). In addition, treatment with bromocriptine a direct full dopamine agonist had a similar effect. Hening et al. (Sleep vol. 27, 3, 2004, 560-583) also reported the dopaminergic treatment of RLS with D2 receptor agonists.

Since then, several other full D2/D3 dopamine agonists used as anti-parkinsonian agents were developed and currently used in the treatment of RLS: Pramipexole, Ropinirole, and Rotigotine (Clemens et al., Advances in Pharmacology, 2019, 84, 79). All dopaminergic agents currently used for the treatment of RLS are full agonists at both the D3 and the D2 receptors.

Description of the Related Art

Neurodegenerative diseases, such as Alzheimer's disease Parkinson's disease and Huntington's disease, share a common cellular and molecular pathogenetic mechanism involving aberrant misfolded protein or peptide aggregation and deposition.

Parkinson's disease, Huntington disease and Alzheimer disease are degenerative disease resulting from the accumulation in Central Nervous System (CNS) neurons of toxic proteins like parkin, huntingtin or beta-amyloid. These proteins can be cleared by various cellular processes among which autophagy is a very effective one (Wang et al International Journal of Molecular Sciences, 2018, 19, 1422-0067).

Autophagy represents a major route for degradation of aggregated cellular proteins and dysfunctional organelles. Recent studies have demonstrated that up-regulation of autophagy can lead to decreased levels of these toxic proteins, and is beneficial in the context of aging and various models of neurodegenerative diseases. Understanding the signalling pathways involved in the regulation of autophagy is crucial to the development of new therapies.

Autophagy might not be effective enough in the above quoted diseases and there is obvious advantage in stimulating it pharmacologically. In this context several authors have reported that dopamine D2 and D3 receptor activation by pramipexole and quinpirole could promote autophagy activation in several cell lines, including primary neurons (Luis-Ravelo et al. Experimental Neurology, 2018, 299, 137-147; Wang et al. Autophagy, 2015, 11, 2057-2073). It was shown in particular that autophagy could be enhanced by pramipexole, a full D3/D2 agonist and its effect was blocked by a pure D3-receptor antagonist. Whereas this indicates that full stimulation of the D3 receptor stimulates autophagy and thereby prevents neuronal degeneration, the effect of a partial D3-receptor agonist was not disclosed (Wang et al. 2018 (as above); Barroso-Chinea et al. Autophagy, 2019, 1-17).

Long-term treatments of these diseases are required. Several issues in the long-term management of the disease were reported, including loss of efficacy over time and several side effects, associated with the D2 and/or D3 full agonists.

Nausea and vomiting are common adverse events due to D2-receptor stimulation by D2 agonists, and the currently used D2/D3 full dopamine agonists promote the loss of behavioral control leading to disorders such as gambling or hypersexuality. Also, augmentation i.e. an exacerbation of symptoms after long-term use of the above agents presumably due to D2 or D3 receptor over-stimulation, is a serious drawback of the presently used dopamine D2/D3 full agonists.

Therefore, there is still a need to provide an efficient treatment for disorders of the central nervous system (CNS), devoid of the above-mentioned side effects.

WO 2007/148208 discloses D3 receptor ligands, which may be antagonists, or inverse agonists or partial agonists or full agonists. Di Ciano et al. (Neuropsychopharmacology 44, 1284-1290, 2019) disclosed that one of the compounds disclosed therein (BP1.4979) is a D3 partial agonist with also D2 antagonist property.

SUMMARY OF THE INVENTION

It has now been surprisingly discovered that this compound with a D3 partial agonist activity and D2 antagonist activity is fully active on disorders of the central nervous system (CNS) although it is a partial D3 agonist. In fact, it had never been suggested that a partial agonist of the D3 receptor could be as effective as a D3 full agonist in treating these disorders.

According to a first object, the present invention concerns compound BP1.4979, of formula:

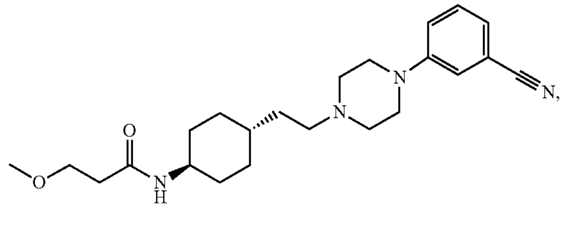 [SMILES: COCCC(=O)N[C@H]1CC[C@H](CCN2CCN(c3cccc(C#N)c3)CC2)CC1]

N-(4-{2-[4-(3-Cyanophenyl)piperazin-1-yl] ethyl}cyclohexyl)-3-methoxypropanamide or a pharmaceutically acceptable salt thereof, or its hydrates, or hydrated salts, or the polymorphic, crystalline structures thereof for use for preventing or treating a disorder of the central nervous system (CNS).

According to an embodiment, said disorder is selected from the restless leg syndrome (RLS), essential tremor, binge eating disorder and neurodegenerative diseases.

According to an embodiment, said disorder is the restless leg syndrome (RLS).

According to an embodiment, said disorder is essential tremor.

According to an embodiment, said disorder is binge eating disorder.

According to an embodiment, said disorder is a neurodegenerative disease.

According to an embodiment, the neurodegenerative disease is selected from Parkinson's disease (PD), Alzheimer's disease (AD) and Huntington's disease (HD).

BP1.4979 is a D3 partial agonist and a D2 antagonist. The structure and process of preparation of BP1.4979 are disclosed in WO 2007/148208.

It was found that it is a highly potent, selective but partial D3-receptor agonist: It is active at the cloned human dopamine D3 receptor with a dissociation constant of 1.2 nM and a 30% intrinsic activity when evaluated in a functional test (namely, mitogenesis). In comparison, it displays only a 661 nM Ki value at the human D2 receptor at which it behaves as a pure antagonist. It is, in addition, inactive at 160 other receptors, channels or enzymes.

Nevertheless, despite its D3 partial agonist profile, it was surprisingly found as potent as dopamine itself or full dopamine D3 agonists.

The activity of a D3 partial agonist, especially to the same extent as that of a D3 full agonist is therefore unexpected.

Additionally, D3 partial agonists involve lesser side effects, such as those involved by the D3 full agonists (augmentation in particular).

Also, D2 antagonists are anti-emetic agents and are thus devoid of the side effects such as nausea and vomiting that are reported for D2 agonists and that are used so far in the treatment of RLS.

Further, the selectivity for D3 receptors with regard to the D2 receptors is highly unexpected as the D2 and D3 receptors are highly homologous proteins, with 78% sequence identity within the transmembrane region. Hence obtaining D3-selective compounds over D2 receptor is notoriously difficult (Chien et al., Science, 330, 1091 (2010)).

As far as RLS is concerned, BP1.4979 was found as potent as dopamine itself or full dopamine agonists in RLS.

The activity of a D3 partial agonist/D2 antagonist was highly unexpected because the activity in RLS had been so far presumably achieved by only fully stimulating preferentially the D3 receptor:

- there is a high preponderance of the inhibitory D3 receptor in the sensory-processing areas of the spinal cord (dorsal horn), which are the gateway for the sensory processing involved in involuntary limb movements that develops during sleep in RLS;
- the non-selective dopamine agonists act as D3-receptor agonists at lower concentrations than at D2 receptors and are also effective in RLS at relatively low dosages compared with dosages for treating Parkinson's disease (in the latter indication presumably via stimulation of the D2 receptor);
- D3-receptor knockout animals display some of the symptoms of RLS.

Therefore based on these observations, it could only be expected that the activity in RLS depends on the affinity towards the D3 receptor, and that a D3 full agonist would involve a higher activity than a D3 partial agonist. Even more, partial agonists can also act as antagonists and hence detrimental to their activity on RLS.

The activity of BP1.4979 was thus highly unexpected.

Similarly PD, AD and HD are chronic diseases in which sustained activity at the D3 receptor is desirable.

As reported above, D3 receptor full agonists promote autophagy mechanism leading to a reduction in aggregates of toxic proteins such as parkin, huntingtin or beta-amyloid, an effect which was blocked by D3 receptor antagonist. As a partial D3 agonist presents an activity with a maximal effect far below the one of full agonist, one could hardly predict to get an efficacy of a partial agonist such as BP1.4979, similar to those of full agonists in these pathologies.

Advantageously, BP1.4979, as a partial agonist, is less prone to induce receptor desensitisation than a full agonist.

Essential tremor is a medical condition characterized by involuntary rhythmic contractions and relaxations. It is either an action (intention) tremor—it intensifies when one tries to use the affected muscles during voluntary movements such as eating and writing—or it is a postural tremor, present with sustained muscle tone. This means that it is distinct from a resting tremor, such as that caused by Parkinson's disease, which is not correlated with movement.

Binge eating disorder (BED) has been introduced as a new disorder in the DSM-V (American Psychiatric Association. (2013). Feeding and eating disorders. In Diagnostic and statistical manual of mental disorders (5th ed.)). BED is characterized by recurrent episodes of binge eating in the absence of regular compensatory behavior such as vomiting or laxative abuse. Related features include eating until uncomfortably full, eating when not physically hungry, eating alone and feelings of depression or guilt. BED is associated with increased psychopathology including depression and personality disorders.

Current medication is performed with Lisdexamfetamine which acts by releasing dopamine in the central nervous system. As such, it behaves like a dopaminergic full agonist.

As used therein:

An «antagonist» refers to a ligand that can bind to a receptor but fails to activate the physiological response of said receptor.

An «agonist» defines a ligand that can bind to a receptor and trigger a physiological response of said receptor.

The term «full agonist» refers to an agonist that binds to and activates a receptor with the maximum response that an agonist can elicit at the receptor.

The term «partial agonist» designates an agonist that also binds to and activates a given receptor, but has only partial efficacy at the receptor, relative to a full agonist, even at maximal receptor occupancy.

The potency of an agonist defines the amount of said agonist to elicit the desired response: it is inversely related to the half-maximal effective concentration (EC50) i.e. the concentration of said agonist which induces a response halfway between the baseline and maximum after a specified exposure time.

Typically, a D3 full agonist elicits a 100% efficacy (or intrinsic activity) relative to a reference full agonist towards said D3 receptor.

Typically, a partial agonist according to the invention elicits an efficacy (or intrinsic activity) of less than 100% relative to a reference full agonist towards the D3 receptor, generally comprised between 10 and 90%, particularly between 20 and 80%.

A reference full agonist towards the D3 receptor is generally chosen from endogenous agonists, such as dopamine. It can also be chosen among known reference full agonists, such as quinelorane or 7-OHDPAT.

Intrinsic activity of a compound towards a receptor can be measured by in vitro tests, such as mitogenesis (Chio et al., Mol. Pharmacol, 45: 51-60, 1994), gene reporter assay (Fitzgerald et al., Anal. Biochem. 275: 54-61, 1999), or calcium flux (Moreland et al., Biochem. Pharmacol. 68:761-772, 2004).

"Ligand" refers to the ability of a compound to bind to a dopaminergic D2 and/or D3 receptor(s) to form a complex therewith.

The term "affinity" illustrates the intermolecular driving force between the ligand (compound) and the receptor. In particular, a high-affinity ligand binding implies that a relatively low concentration of a ligand is adequate to maximally occupy a ligand-binding site of the D2 and/or D3 receptor(s), whereas a low-affinity binding implies that a relatively high concentration of a ligand is required before the binding site is maximally occupied.

As used herein, "pharmaceutically acceptable salts" refer to derivatives of the disclosed compounds wherein the parent compound is modified by making acid or base salts thereof. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propanoic, succinic, tartaric, citric, methanesulfonic, benzenesulfonic, glucuronic, glutamic, benzoic, salicylic, toluenesulfonic, oxalic, fumaric, maleic, and the like. Further addition salts include ammonium salts such as tromethamine, meglumine, epolamine, etc., metal salts such as sodium, potassium, calcium, zinc or magnesium. Hydrochloride and oxalate salts are preferred.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, non-aqueous media like ether, ethyl acetate, ethanol, isopropanol, or acetonitrile are preferred. Lists of suitable salts are found in *Remington's Pharmaceutical Sciences*, 17$^{th}$ ed., Mack Publishing Company, Easton, PA, 1985, p. 1418, the disclosure of which is hereby incorporated by reference.

The activity of a compound in RLS can be predicted by its efficacy in relevant animal models. Animal models predictive of RLS are described by Ondo W G et al. (Movement Disorders, 2000, 15, 154-158) and Clemens S et al. (J. Neurosci. 2004, 24, 11337-11345).

In particular, the invention provides an in vivo assay predictive of the activity in RLS, such as in rodents. It is disclosed a method for predicting the activity in RLS for test compounds, comprising running said compound in an electrophysiological model of monosynaptic spinal cord reflex in the rat.

More particularly, it discloses an in vivo screening method for identifying a drug candidate for treating RLS, said method comprising conducting an in vivo assay comprising:

running an electrophysiological model of monosynaptic spinal cord reflex in a rodent with a test compound and a reference compound;

comparing the measured response of the test compound with the measured response of a reference compound in said test in a given concentration;

selecting said test compound if its activity is higher than that of the test compound.

According to an embodiment, this model comprises:

stimulating the sensitive root and recording the resulting action potential in the motor root;

applying in the dorsal horn a reference compound or a test compound assessing the inhibition of the monosynaptic reflex with the reference compound and the test compound.

According to an embodiment, the measured response is the inhibition of the synaptic transmission.

More particularly, the response measured in this test reflects the inhibitory modulatory input of a descending hypothalamo-dorsospinal dopaminergic neuronal pathway, which appears defective in RLS, resulting in exaggeration of the reflex in this disease.

According to an embodiment, the reference compound is a full dopamine D2/D3 receptor agonist, such as dopamine or Pramipexole (currently used in RLS), or 7-OHDPAT, a D3 receptor full agonist.

According to an embodiment, said test compound is a D3 partial agonist.

The activity of BP1.4979 (partial D3 agonist) against RLS was shown to be equivalent to that of Rotigotine (a mixed D2 and D3 full agonist) in a double-blind versus placebo clinical trial. Absence of common side-effects (nausea and vomiting) associated with the current treatments has been noted during this clinical trial.

According to a further object, the present invention concerns a method of treating and/or preventing RLS in a patient in the need of it, comprising administering a D3 partial agonist as defined above to said patient.

The activity of BP1.4979 (partial D3 agonist) against binge eating disorder has been shown using a rodent model of this disease, namely sucrose bingeing in the rat.

The activity of BP1.4979 (partial D3 agonist) against excessive food consumption related to binge eating disorder has been measured in clinical trial related to smoke cessation. Upon smoke cessation, the smoker volunteers who received BP1.4979 gained less weight than those receiving placebo. This was dose-related showing that the effect is related to the compound.

According to a further object, the present invention concerns a method of treating and/or preventing binge eating disorder in a patient in the need of it, comprising administering a D3 partial agonist as defined above to said patient.

According to a further object, the present invention also concerns a method of treating and/or preventing disorders of the central nervous system (CNS) as defined above in a patient in the need thereof, comprising administering a D3 partial agonist as defined above to said patient.

The identification of those subjects who are in need of treatment of herein-described diseases and conditions is well within the ability and knowledge of one skilled in the art. A clinician skilled in the art can readily identify, by the use of clinical tests, physical examination, genetic tests and medical/family history, those subjects who are in need of such treatment.

According to an embodiment, the recommended dose of BP1.4979 may be comprised between 10 and 100 mg and preferably 10 and 15 mg B.I.D (bis in die). However, alternative therapeutically effective amount of BP1.4979 can be readily determined by the attending diagnostician, as one skilled in the art, by the use of conventional techniques and by observing results obtained under analogous circumstances. In determining the therapeutically effective amount, a number of factors are considered by the attending diagnostician, including, but not limited to: the species of subject; its size, age, and general health; the specific disease involved; the degree of involvement or the severity of the disease; the response of the individual subject; the particular compound administered; the mode of administration; the bioavailability characteristic of the preparation administered; the dose regimen selected; the use of concomitant medication; and other relevant circumstances. The amount of BP1.4979 which is required to achieve the desired biological effect, will vary depending upon a number of factors, including the dosage of the drug to be administered, the chemical characteristics (e.g. hydrophobicity) of the compounds employed, the potency of the compounds, the type of disease, the diseased state of the patient and the route of administration.

"Pharmaceutically" or "pharmaceutically acceptable" refer to molecular entities and compositions that do not produce an adverse, allergic or other untoward reaction when administered to an animal, or a human, as appropriate.

As used herein, "pharmaceutically acceptable carrier" includes any diluents, adjuvants, excipients, or vehicles, such as preserving agents, fillers, disintegrating agents, wetting agents, emulsifying agents, suspending agents, solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

In the context of the invention, the term "treating" or "treatment", as used herein, means reversing, alleviating, inhibiting the progress of, or preventing the disorder or condition to which such term applies, or one or more symptoms of such disorder or condition.

"Therapeutically effective amount" means an amount of a compound/medicament according to the present invention effective in producing the desired therapeutic effect.

According to the invention, the term "patient", or "patient in need thereof", is intended for a human or non-human mammal affected or likely to be affected with a neuropsychological disorder. Preferably, the patient is a human.

In general terms, the compounds of this invention may be provided in an aqueous physiological buffer solution containing 0.1 to 10% w/v compound for parenteral administration. Typical dose ranges are from 1 μg/kg to 0.1 g/kg of body weight per day; a preferred dose range is from 0.01 mg/kg to 10 mg/kg of body weight per day. A preferred daily dose for adult humans includes 5, 50, 100 and 200 mg, and an equivalent dose in a human child. The preferred dosage of drug to be administered is likely to depend on such variables as the type and extent of progression of the disease or disorder, the overall health status of the particular patient, the relative biological efficacy of the compound selected, and formulation of the compound excipient, and its route of administration.

The compounds of the present invention are capable of being administered in unit dose forms, wherein the term "unit dose" means a single dose which is capable of being administered to a patient, and which can be readily handled and packaged, remaining as a physically and chemically stable unit dose comprising either the active compound itself, or as a pharmaceutically acceptable composition, as described hereinafter. As such, typical daily dose ranges are from 0.01 to 10 mg/kg of body weight. By way of general guidance, unit doses for humans range from 1 mg to 100 mg per day. Preferably, the unit dose range is from 1 to 500 mg administered one to four times a day, and even more preferably from 10 mg to 300 mg, twice a day. Compounds provided herein can be formulated into pharmaceutical compositions by admixture with one or more pharmaceutically acceptable excipients. Such compositions may be prepared for use in oral administration, particularly in the form of tablets or capsules; or parenteral administration, particularly in the form of liquid solutions, suspensions or emulsions; or intranasally, particularly in the form of powders, nasal drops, or aerosols; or dermally, for example, topically or via trans-dermal patches. The compositions may conveniently be administered in unit dosage form and may be prepared by any of the methods well known in the pharmaceutical art, for example, as described in *Remington: The Science and Practice of Pharmacy,* $20^{th}$ ed.; Gennaro, A. R., Ed.; Lippincott Williams & Wilkins: Philadelphia, PA, 2000. Pharmaceutically compatible binding agents and/or adjuvant materials can be included as part of the composition. Oral compositions will generally include an inert diluent carrier or an edible carrier.

The tablets, pills, powders, capsules, troches and the like can contain one or more of any of the following ingredients, or compounds of a similar nature: a binder such as microcrystalline cellulose, or gum tragacanth; a diluent such as starch or lactose; a disintegrant such as starch and cellulose derivatives; a lubricant such as magnesium stearate; a glidant such as colloidal silicon dioxide; a sweetening agent such as sucrose or saccharin; or a flavoring agent such as peppermint, or methyl salicylate. Capsules can be in the form of a hard capsule or soft capsule, which are generally made from gelatin blends optionally blended with plasticizers, as well as a starch capsule. In addition, dosage unit forms can contain various other materials that modify the physical form of the dosage unit, for example, coatings of sugar, shellac, or enteric agents. Other oral dosage forms syrup or elixir may contain sweetening agents, preservatives, dyes, colorings, and flavorings. In addition, the active compounds may be incorporated into fast dissolve, modified-release or sustained-release preparations and formulations, and wherein such sustained-release formulations are preferably bi-modal.

Preferred formulations include pharmaceutical compositions in which a compound of the present invention is formulated for oral or parenteral administration, or more preferably those in which a compound of the present invention is formulated as a tablet. Preferred tablets contain lactose, cornstarch, magnesium silicate, croscarmellose sodium, povidone, magnesium stearate, or talc in any combination. It is also an aspect of the present disclosure that a compound of the present invention may be incorporated into a food product or a liquid.

Liquid preparations for administration include sterile aqueous or non-aqueous solutions, suspensions, and emulsions. The liquid compositions may also include binders, buffers, preservatives, chelating agents, sweetening, flavoring and coloring agents, and the like. Non-aqueous solvents include alcohols, propylene glycol, polyethylene glycol, vegetable oils such as olive oil, and organic esters such as ethyl oleate. Aqueous carriers include mixtures of alcohols and water, buffered media, and saline. In particular, biocompatible, biodegradable lactide polymer, lactide/glycolide copolymer, or polyoxyethylene-polyoxypropylene copolymers may be useful excipients to control the release of the active compounds. Intravenous vehicles can include fluid and nutrient replenishers, electrolyte replenishers, such as those based on Ringer's dextrose, and the like. Other potentially useful parenteral delivery systems for these active compounds include ethylene-vinyl acetate copolymer particles, osmotic pumps, implantable infusion systems, and liposomes.

Alternative modes of administration include formulations for inhalation, which include such means as dry powder, aerosol, or drops. They may be aqueous solutions containing, for example, polyoxyethylene-9-lauryl ether, glycocholate and deoxycholate, or oily solutions for administration in the form of nasal drops, or as a gel to be applied intranasally. Formulations for buccal administration include, for example, lozenges or pastilles and may also include a flavored base, such as sucrose or acacia, and other excipients such as glycocholate. Formulations suitable for rectal administration are preferably presented as unit-dose suppositories, with a solid based carrier, such as cocoa butter, and may include a salicylate. Formulations for topical application to the skin preferably take the form of an ointment, cream, lotion, paste, gel, spray, aerosol, or oil. Carriers which can be used include petroleum jelly, lanolin, polyethylene glycols, alcohols, or their combinations. Formulations suitable for transdermal administration can be presented as discrete patches and can be lipophilic emulsions or buffered, aqueous solutions, dissolved and/or dispersed in a polymer or an adhesive.

DESCRIPTION OF THE PREFERRED EMBODIMENTS

Figure 1:
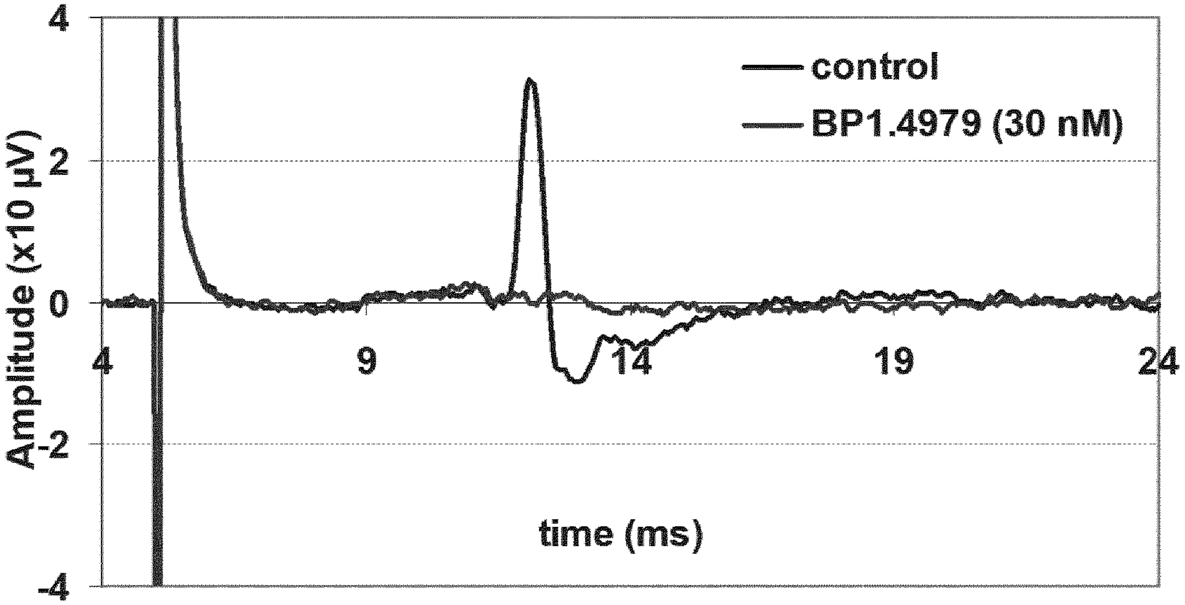
FIG. 1 illustrates the effects of BP1.4979 (30 nM) on the amplitude of the response of ventral root elicited by a supra-liminar stimulation (40 V, 50 μs) of the dorsal root, showing the action potential, mean of 15 recordings each, in control and BP1.4979-perfused conditions.

The present invention is further illustrated by the following non-limiting examples:

EXAMPLES

The efficacy of BP1.4979 and the three currently used dopamine agonists on human dopamine D2 and D3 receptors was assessed on the following systems.

Mitogenesis Assay of D3-Receptor Activation

Chinese hamster ovary (CHO) cells stably expressing the human dopamine D3 receptor were plated overnight in 96-well plates. Cells were then washed with serum-free medium, and incubated 20 h with various concentrations of ligands. Tritiated thymidine was added for a 4 hour-pulse. Then, the cells were detached with trypsin/EDTA, transferred in GF/C multiscreen microplates, rinsed with ice-cold PBS and ethanol and dried. [$^3$H]-Thymidine incorporation was measured by liquid scintillation in a MicroBeta counter.

Results are expressed as percentage of the maximal [$^3$H]-thymidine incorporation yielded with the full agonist quinelorane.

In this test BP1.4979 behaved as a partial agonist (intrinsic activity of 30%, EC50 of 0.7 nM) whereas Pramipexole and Ropinirole were full agonists with EC50 of 0.6 and 0.7 nM, respectively.

GTPγ$^{35}$S Binding Assay at D3 Dopamine Receptor

Thawed membranes from CHO cells stably expressing human D3 receptor were diluted at a final concentration of 5 μg/180 μL/well in a binding buffer containing HEPES 50 mM, $MgCl_2$ 3 mM, NaCl 140 mM, GDP 4 μM, pH=7.4 and distributed in 96 well polystyrene microplate. GTPγ[$^{35}$S] labelled ligand (0.2-0.3 nM) is added for additional 30 minutes at room temperature. After transfer in a Millipore GF/C HTS® microplate, the filtration of the reactional mix followed by a three time 250 μl wash put an end to the reaction. The filter-bound radioactivity was measured in a liquid scintillation counter Microbeta with 70 μl of scintillation fluid.

In this test, BP1.4979 displays a too weak partial activity (<5%) to be measurable. This shows that BP1.4979 is clearly not a full agonist. The full agonist pramipexole was as efficient as dopamine, the full agonist reference in the GTPγ[$^{35}$S] assay.

In addition, the efficacy of the compounds was compared on the activation of the human dopamine D2 receptor.

Calcium Fluxes Assay of D2-Receptor Activation/Inhibition

HEK293 cells expressing the human dopamine D2 short isoform were used to evaluate the potential agonist property of test compounds. Cells were loaded with Fluo-4-AM solution supplemented with sulfinpyrazone then plated in a 96-well plate and introduced in a FLEX station for fluorescence measurement following calcium transients.

Responses were calculated as the maximum minus the minimum fluorescence counts (Fmax−Fmin). Results are given as percent of the maximal response elicited by the reference full agonist quinelorane.

In this test, Pramipexole, Rotigotine, and Ropinirole behaved as full agonists with EC50 values of 5.4, 0.3, and 20 nM, respectively. In contrast, BP1.4979 failed to activate the receptor at concentrations up to 1,000 nM and was even able to block completely the effect of dopamine or agonists.

In summary, BP 1.4979 clearly differs from the three dopamine ligands currently used in the treatment of RLS: they are potent D3R and D2R full agonists whereas BP 1.4979 is a partial D3R agonist and inactive as agonist at the D2R.

Effects of BP1.4979 in a Rat Model of RLS

RLS is believed to reflect an abnormal sensitivity of spinal stretch reflexes. These reflexes are modulated in an inhibitory fashion by dopamine released in the dorsal horn from a descending dopaminergic projection arising from A11 dopamine cells in the hypothalamus.

Therefore, it was of interest to investigate BP1.4979 effects in the monosynaptic response in the isolated spinal cord, an electrophysiological model of the stretch reflex, which could account for some aspects of the mechanisms implied in the RLS. Electrophysiological responses i.e. motor action potentials recorded on the ventral root of isolated spinal cord from rat pups following stimulation of the dorsal root were analyzed.

Using a threshold intensity of stimulation (40 V, 50 μs), BP1.4979 was tested at 3 concentrations (30, 100, and 300 nM) and the response recorded.

Figure 2:
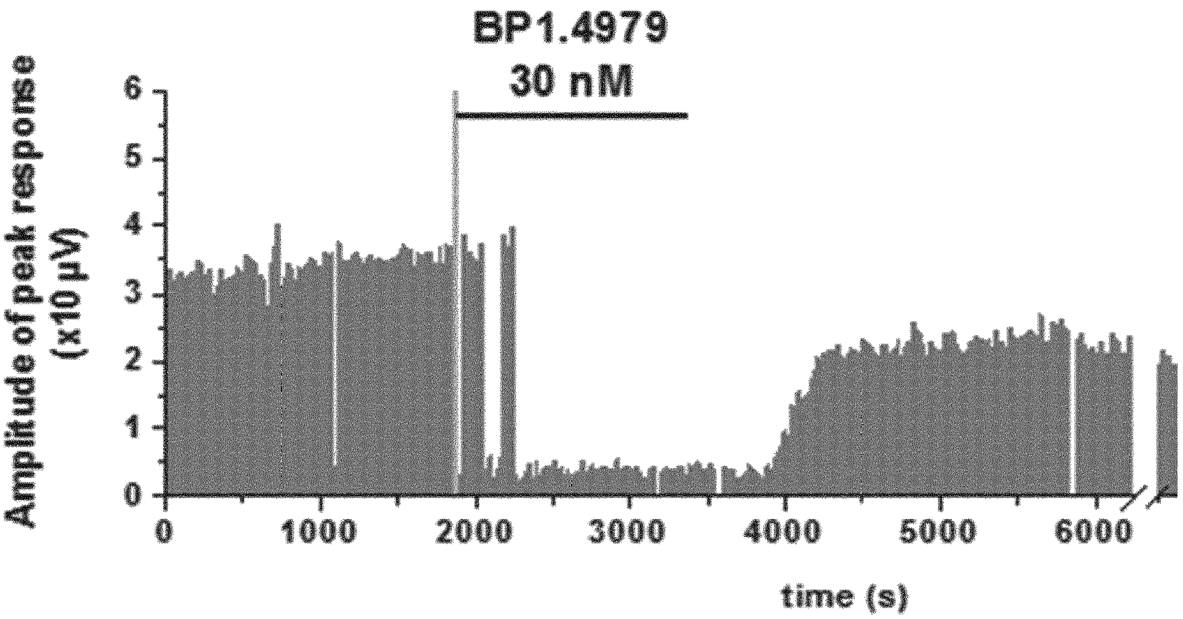
FIG. 2 illustrates the effects of BP1.4979 (30 nM) on the amplitude of the response of ventral root elicited by a supra-liminar stimulation (40 V, 50 μs) of the dorsal root, showing the amplitude of peak response over time.

The results are reported in FIGS. 1 and 2. At a 30 nM concentration, BP1.4979 inhibited fully the synaptic transmission for these fibers i.e. to the same extent as dopamine or a full dopamine D2/D3 receptor agonist such as Pramipexole and 7-OHDPAT.

Dopamine, Pramipexole and 7-OHDPAT resulted in a total or nearly total inhibition of the monosynaptic reflex. Surprisingly, application of BP1.4979 in nanomolar concentrations instead of dopamine or full dopamine agonists elicits inhibitions of the same amplitude as the latters.

In another series of experiments, BP1.4979 dose dependently inhibited the amplitude of the post-synaptic response measured on the ventral root of the spinal cord following the supraliminar stimulation of the dorsal root and this effect was prevented in the presence of the dopamine $D_3$ antagonist BP1.4096 (example 107 of WO 2007/148208) which, by itself, was devoid of effect.

In summary, although it is a partial D3-receptor agonist and D2-receptor antagonist, which differentiates it from agents typically used in RLS, BP1.4979 unexpectedly appeared to be fully active on a model of this disease.

Clinical Studies: Efficacy of BP1.4979 in Restless Legs Syndrome (Randomized, Double Blind Parallel Groups Sequential, Placebo Controlled, Clinical Trial)

The double-blind trial was conducted on 29 patients. BP1.4979 was administered at a dose of 15 mg twice a day for two weeks and its effect compared with that of placebo.

BP1.4979 demonstrated a significant efficacy in RLS patients versus placebo using the PLMS index (Periodic Limb Movements per hour of Sleep).

The periodic limb movement index was significantly decreased after therapy with BP1.4979.

This was compared with rotigotine, an existing reference compound used in the treatment of RLS (Bogan et al Clinical Therapeutics/Volume 36, Number 3, 2014).

Wu et al (2018), PLoS ONE 13(4): e0195473 reported the PLMS index with rotigotine.

Results indicate that the value (PLMS index lowering) obtained with BP1.4979 is similar to the value reported by Wu et al in the rotigotine group.

This is highly surprising as it shows that BP1.4979 appears as effective as a D3R and D2R full agonist in the RLS pathology.

Furthermore, no patient reported any symptom related to nausea nor did had vomiting episodes. This absence of these side-effects usually observed with Pramipexole, Ropinirole, and Rotigotine impressively improved the benefit/risk ratio for the treatment of RLS with BP1.4979.

In conclusion, the clinical study confirms the interest of a D3R partial agonist in RLS.

Activity of BP1.4979 in a Rodent Model of Binge Eating Disorder

Female Sprague-Dawley rats (225-250 g) were given 12-h access to an aqueous 10% sucrose solution and lab chow, followed by 12 h of deprivation daily for three or more weeks (i.e., daily intermittent sucrose and chow). Control animals had ad libitum access to sucrose solution and lab chow. After such a regimen, these rats with intermittent diets develop a binge eating behavior and enter a state that resembles drug dependence on several dimensions: escalation of daily sucrose intake, withdrawal behavior, craving, and cross-sensitization (N. M. Avena, P. Rada, and B. G. Hoebel, "Evidence for sugar addiction: behavioral and neurochemical effects of intermittent, excessive sugar intake.," Neurosci Biobehav Rev. 2008; 32(1):20-39). On the day of the experiment, rats were treated 0.3 and 1 mg/kg, i.p. of BP1.4979 or with vehicle (n=8 per group) 30 min before re-introduction of sucrose and chow, which consumption was subsequently measured.

Absence of Weight Gain During Smoking Cessation by Volunteers Receiving BP1.4979

In a double blind clinical trial, healthy smokers had to stop smoking while receiving placebo (n=55) or BP1.4979 3 mg (n=52), 10 mg (n=53), or 15 mg (n=58) once a day.

After twelve weeks, the volunteers receiving placebo gained 1.0 kg whereas those receiving BP1.4979 experienced a lower weight increase: 0.9 kg (respectively 0.5 kg) for the group receiving 3 mg (respectively 10 mg) or no weight increase (0.0 kg for the group receiving 15 mg).

Twelve further weeks after the end of treatment, a similar trend was observed. Compared to the weight before treatment, the volunteers receiving placebo gained 2.3 kg whereas those receiving BP1.4979 experienced a lower weight increase of 2.0 kg, 1.4 kg and 0.2 kg for the groups receiving 3 mg, 10 mg and 15 mg, respectively.

The invention claimed is:

1. A method for treating restless leg syndrome (RLS), comprising administering the compound BP1.4979, of formula:

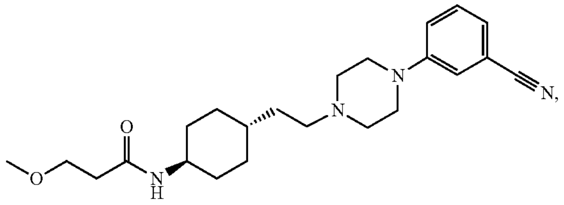 [SMILES: COCCC(=O)N[C@H]1CC[C@H](CCN2CCN(c3cccc(C#N)c3)CC2)CC1]

N-(4-{2-[4-(3-Cyanophenyl) piperazin-1-yl] ethyl}cyclohexyl)-3-methoxypropanamide or a pharmaceutically acceptable salt thereof, or crystalline structures thereof, comprising administering said compound at a dose comprised between 10 and 15 mg B.I.D. (bis in die).

2. A method for treating binge eating disorder comprising administering the compound BP1.4979, of formula:

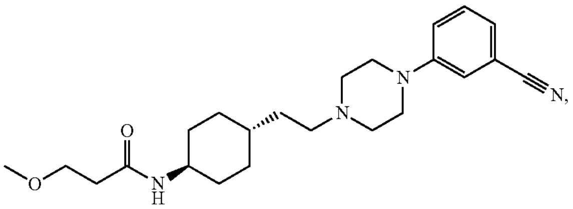 [SMILES: COCCC(=O)N[C@H]1CC[C@H](CCN2CCN(c3cccc(C#N)c3)CC2)CC1]

N-(4-{2-[4-(3-Cyanophenyl) piperazin-1-yl] ethyl}cyclohexyl)-3-methoxypropanamide or a pharmaceutically acceptable salt thereof, or crystalline structures thereof.

3. The method according to claim 2, comprising administering said compound at a dose comprised between 10 and 100 mg B.I.D. (bis in die).

4. The method according to claim 2, comprising administering said compound at a dose comprised between 10 and 15 mg B.I.D. (bis in die).

* * * * *